United States Patent [19]

Bowlin, Jr.

[11] Patent Number: 5,451,379
[45] Date of Patent: Sep. 19, 1995

[54] STERILIZATION CASSETTE FOR DENTAL INSTRUMENTS

[76] Inventor: Eugene F. Bowlin, Jr., 2925 Comice Way, Medford, Oreg. 97504

[21] Appl. No.: 184,352

[22] Filed: Jan. 21, 1994

Related U.S. Application Data

[63] Continuation of Ser. No. 986,994, Dec. 7, 1992, abandoned.

[51] Int. Cl.⁶ .............................................. A61L 2/06
[52] U.S. Cl. .................................... 422/297; 422/300;
422/292; 206/370; 206/560; 206/564; 206/565;
220/315; 220/334; 292/218; 292/DIG. 31
[58] Field of Search ................ 422/102, 292, 297, 300,
422/310; 206/63.5, 263, 370, 560, 564, 565;
220/324, 244, 306, 315, 334; 292/218, 251, 203,
DIG. 31

[56] References Cited

U.S. PATENT DOCUMENTS

| | | | |
|---|---|---|---|
| D. 295,074 | 4/1988 | Jerge et al. | D24/9 |
| D. 295,075 | 4/1988 | Jerge et al. | D24/9 |
| 2,740,683 | 4/1956 | June | 206/263 X |
| 2,991,904 | 7/1961 | Carideo | 292/251 |
| 3,062,365 | 11/1962 | Fletcher | 206/263 X |
| 3,123,389 | 3/1964 | Biesecker | 292/218 |
| 3,576,340 | 4/1971 | Jones | 220/324 X |
| 3,636,413 | 1/1972 | Ditthardt et al. | 220/324 X |
| 4,061,371 | 12/1977 | Prather et al. | 292/198 |
| 4,541,992 | 9/1985 | Jerge et al. | 422/300 |
| 4,615,464 | 10/1986 | Byrns | 220/469 |
| 4,774,063 | 9/1988 | Runnells | 422/297 |
| 4,798,292 | 1/1989 | Hauze | 206/439 |
| 4,820,499 | 4/1989 | Taschner | 422/310 |
| 4,854,475 | 8/1989 | Riihimaki et al. | 220/337 |
| 4,959,199 | 9/1990 | Brewer | 422/300 |
| 4,989,747 | 2/1991 | Demurger | 220/324 |
| 5,040,834 | 8/1991 | Kahl et al. | 292/204 |
| 5,084,251 | 1/1992 | Thomas | 422/300 |
| 5,098,676 | 3/1992 | Brooks | 422/292 |
| 5,100,015 | 3/1992 | Vanderstuyf | 220/326 |
| 5,211,915 | 5/1993 | Mönch | 422/102 |
| 5,215,726 | 6/1993 | Kudla et al. | 422/297 |

*Primary Examiner*—James C. Housel
*Assistant Examiner*—Harold Y. Pyon
*Attorney, Agent, or Firm*—Klarquist Sparkman Campbell Leigh & Whinston

[57] ABSTRACT

A dental instrument sterilization cassette securely retains dental instruments on a cover and tray of a perforated housing. Within the cover and tray, the dental instruments are received on open cradled supports. A holddown device with a resilient covering is placed over the cradled instruments, and held in place by anchors attached to the cover and tray. The cradled supports and the resilient holddown device provide secure retention for a range of instrument sizes when the cassette is in either an opened or closed position. A cassette latching mechanism with a recessed latch actuator on the cassette cover provides positive latching of the instrument cassette.

12 Claims, 3 Drawing Sheets

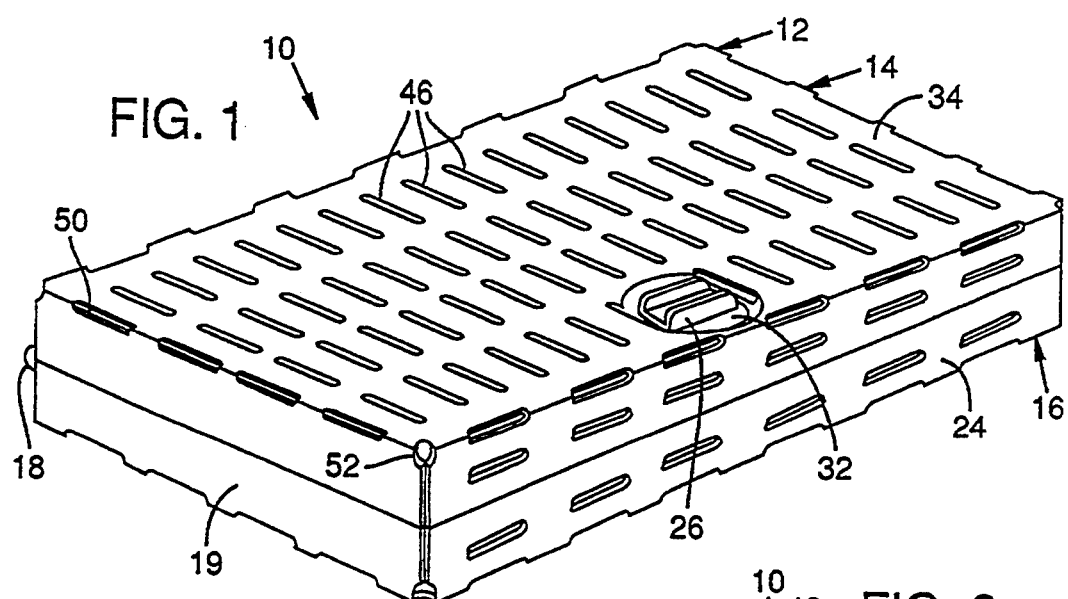
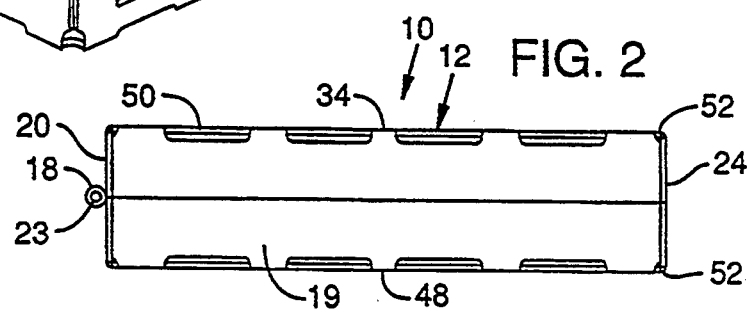
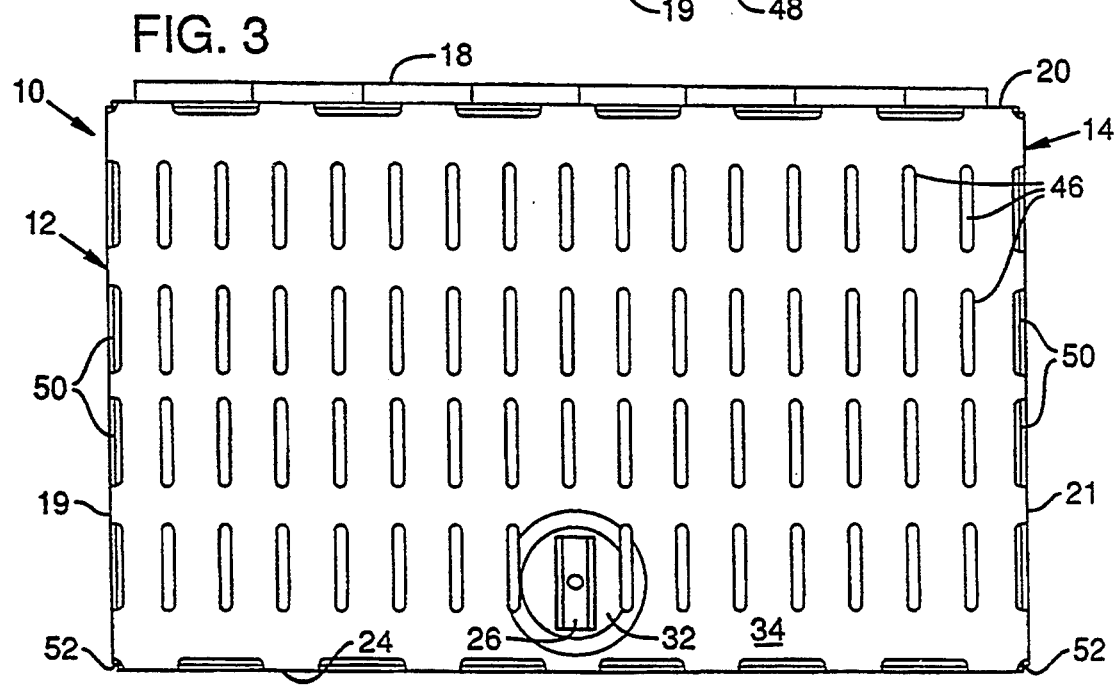

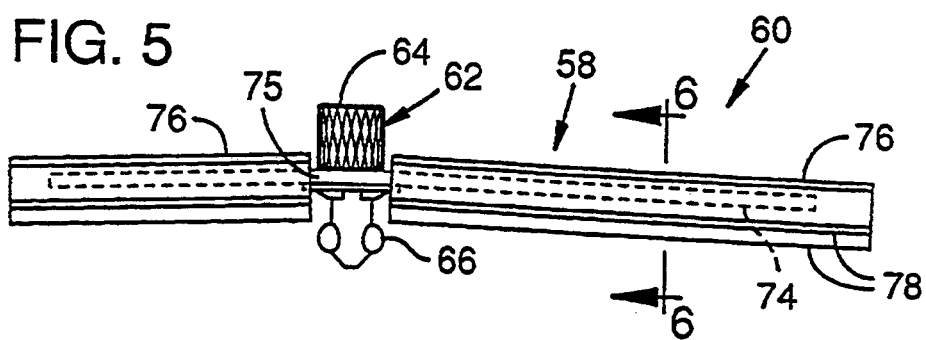
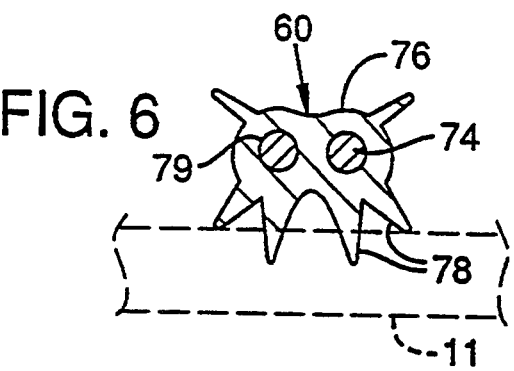
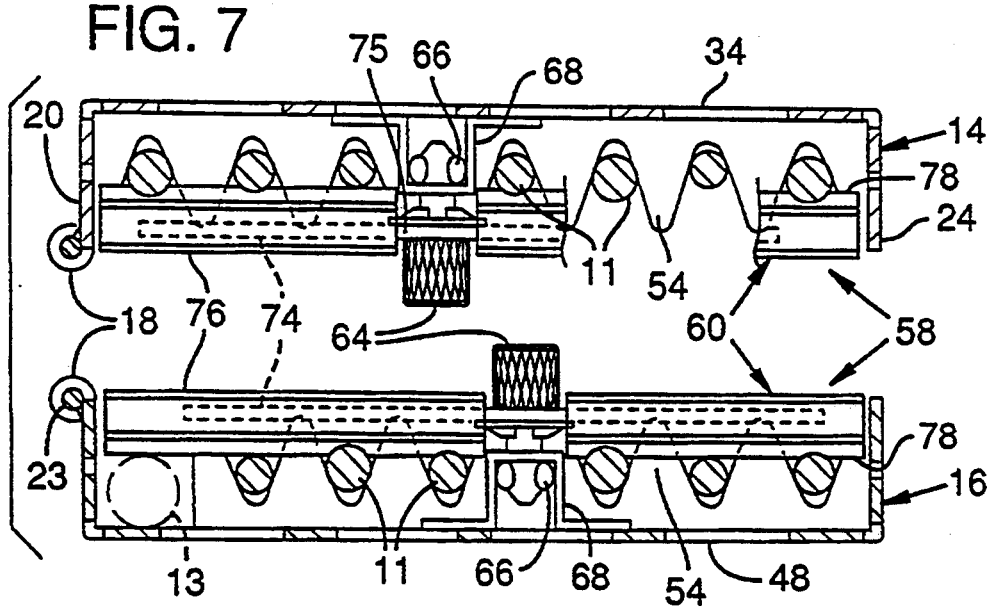
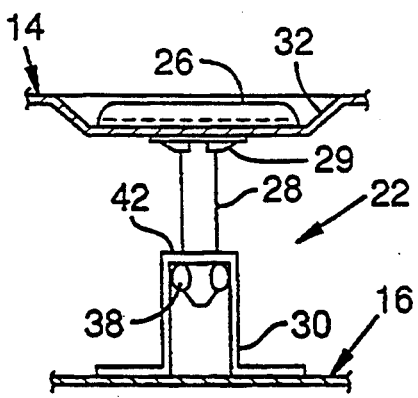

STERILIZATION CASSETTE FOR DENTAL INSTRUMENTS

This application is a continuation of application Ser. No. 07/986,994, filed on Dec. 7, 1992, now abandoned.

BACKGROUND OF THE INVENTION

1. Field of the Invention

The present invention relates to cassettes for the storage and sterilization of dental and surgical instruments.

2. Description of the Prior Art

Dental instrument sterilization cassettes are devices which hold contaminated dental instruments during a sterilization process. Contaminated instruments are stored within a sterilization cassette, which is then placed in a sterilizer and subjected to a flow of sterilizing vapor. Sterilization cassettes are usually provided with a series of slots or holes to allow the flow of sterilizing vapor to pass through the cassette and over the instruments.

In today's dental practice, an ever-increasing volume of contaminated dental instruments requires effective sterilization. Given the rapidly increasing cost of dental services, and the heightened competition within the dental profession, the need for cost effective instrument sterilization is clear. In improving instrument sterilization efficiency, some important factors include: improved instrument storage capacity, convenient cassette retention of a range of instrument sizes, cassette capacity to serve the sterilized instruments to dental personnel in an operating theatre, and thinner cassette profiles (to increase cassette stacking efficiency within an autoclave).

Another factor, the advent of the AIDS epidemic, has focussed attention on instrument sterilization in another way. In particular, the danger inherent in AIDS-contaminated blood has created a demand for instrument sterilization cassettes which pose the lowest risk of accidentally exposing health care workers to contaminated instruments. Dependable instrument retention and cassette latching mechanisms are the principal factors in addressing this need.

As regards instrument sterilization efficiency, instrument storage capacity is a primary consideration. For example, the device shown in U.S. Pat. No. 5,084,251 of Thomas stores instruments in only one half of the sterilization cassette, yielding a relatively low instrument storage capacity. On the other hand, U.S. Pat. No. 4,959,199 of Brewer shows a sterilization cassette with instruments stored in both cassette halves, with an attendant increase in instrument storage capacity.

These instrument sterilization cassettes also reveal the usual deficiencies in approaches to instrument retention. In the opened Thomas cassette, the instruments always rest loosely on the supports, resulting in a vulnerability to spillage. When the Thomas cassette is closed, the instruments are secured in the supports by retaining bars attached to the upper half of the cassette.

Alternatively, the Brewer cassette has instruments stored on both halves in removable trays with "snap-in" supports. These supports only accept instruments sized to fit into the non-adjustable "snap-in" retainers. Thus, if different sized instruments are to be stored, Brewer requires a replacement tray fitted with appropriately sized "snap-ins." The "snap-in" supports are capable of insecure, loose acceptance of instruments smaller than the "snap-in" size, thereby creating a risk of instrument spillage.

Furthermore, these instrument storage and retention schemes also may detract from the application of these cassettes as instrument servers. In this role, an opened instrument sterilization cassette, situated on a working surface in an operating theatre, presents the instruments for removal as needed by a dental assistant or dentist. For this application, the Thomas cassette is spacially inefficient in only providing storage on one half of the cassette. The Brewer cassette is not optimal because of the concentration required to pull the stored instruments out of the "snap-in" retainers.

Turning to the need to reduce the exposure of health personnel to contaminated instruments, the dependability of cassette latching mechanisms becomes paramount. For instance, since the tops and bottoms of the Brewer and Thomas cassettes are not structurally obvious, these cassettes could be prone to upside-down opening. In this event, the loose instruments in the opened Thomas cassette could spill.

Brewer, on the other hand, shows intermediate locking plates providing additional security against spillage in the case of accidental opening. However, since these plates are not required to secure the instruments within the "snap-in" retainers, they may be forgotten by a health worker. Thus, any inappropriately small instruments stored in the Brewer "snap-ins" could be vulnerable to this type of spillage.

In addition, the toughness and durability of cassette latching mechanisms are key in avoiding accidental openings. These references' latch mechanisms are situated on the cassette exteriors, and are thus subject to abuse and possible accidental opening. Brewer's latch is particularly susceptible to inadvertent opening since a mere depression of an exposed hinge tongue causes the latch to release.

Finally, the references also show perforated cassette bodies which do not optimally drain away instrument debris during the sterilization operation. The referenced cassettes show numerous corner surfaces where debris from the sterilized instruments could catch and collect. Such debris retention is undesirable in any sterilization vessel.

Additional dental instrument sterilization cassettes are shown in U.S. Pat. No. 4,541,992 of Jerge et al., and U.S. Pat. No. 4,854,475 of Riihimaki.

SUMMARY OF THE INVENTION

In light of the disadvantages in the prior art, one objective of the present invention is to provide a cassette with an improved instrument storage efficiency.

Another important objective of this invention is to provide an instrument sterilization cassette which minimizes the chances of dental personnel inadvertently coming into contact with contaminated instruments by retaining instruments more safely than prior such cassettes.

Another objective of this invention is to provide for secure retention of the instruments within the instrument supports when the cassette is in an open position.

An additional objective of this invention is to provide an instrument sterilization cassette which efficiently serves the sterilized instruments in the operating theatre.

Still an additional objective of this invention is to provide an instrument retention mechanism which can accommodate a variety of instrument sizes while being relatively insusceptible to inadvertent instrument loss.

Yet another objective of the present invention is to provide a dependable cassette latching mechanism which is relatively invulnerable to accidental opening.

One more objective of this invention, is to provide a cassette wherein the top surface of the cassette is structurally defined.

Still another objective of this invention is to provide an instrument sterilization cassette housing with a pattern of drainage openings which optimizes the draining away of instrument debris during the sterilization process while minimizing the opportunity for sharp-tipped instruments to protrude through such openings.

Other objects will be apparent from the detailed description of the present invention.

An instrument sterilization cassette in accordance with one aspect of the present invention has a cover attached to a tray by a hinge. The cover and tray make up a perforated housing with openings on the faces, corners, and along the edges to enable effective drainage of instrument debris. Variously sized dental instruments are loosely cradled on supports in both the cover and tray portions of the cassette. A holddown device is provided to securely fasten the instruments within their cradle supports when the cassette is in an opened or closed position. The holddown device includes a retention bar placed over the cradled instruments and anchored onto the cover or tray by a holddown anchor. The retention bars residing on the cover and tray are offset with respect to each other so as to avoid interference when the cassette is in a closed position.

The cassette has a positive latching mechanism with a rotatable, protectively-recessed latch actuator defining the top of the cassette. A latch stem, distally provided with latch teeth, extends from the latch actuator into the interior of the cassette, and is received by a latch anchor residing in the tray. To positively latch the tray and cover in a closed position, the latch actuator is rotated to latch the latch teeth within the latch anchor.

BRIEF DESCRIPTION OF THE DRAWINGS

FIG. 1 is a perspective view of a dental instrument sterilization cassette in accordance with a preferred embodiment of the present invention as viewed from above toward the top, front and one side.

FIG. 2 is an elevational side view of the cassette of FIG. 1.

FIG. 3 is a top plan view of the cassette of FIG. 1.

FIG. 5 is an elevational view of a holddown device of the preferred embodiment.

FIG. 6 is a cross-sectional view taken along line 6—6 of FIG. 5.

FIG. 7 is an exploded cross-sectional view taken along line 7—7 of FIG. 4.

FIG. 8 is a elevational cross-sectional view of the latching mechanism of a preferred embodiment of the present embodiment.

DETAILED DESCRIPTION OF THE ILLUSTRATED EMBODIMENT

Figure 4:
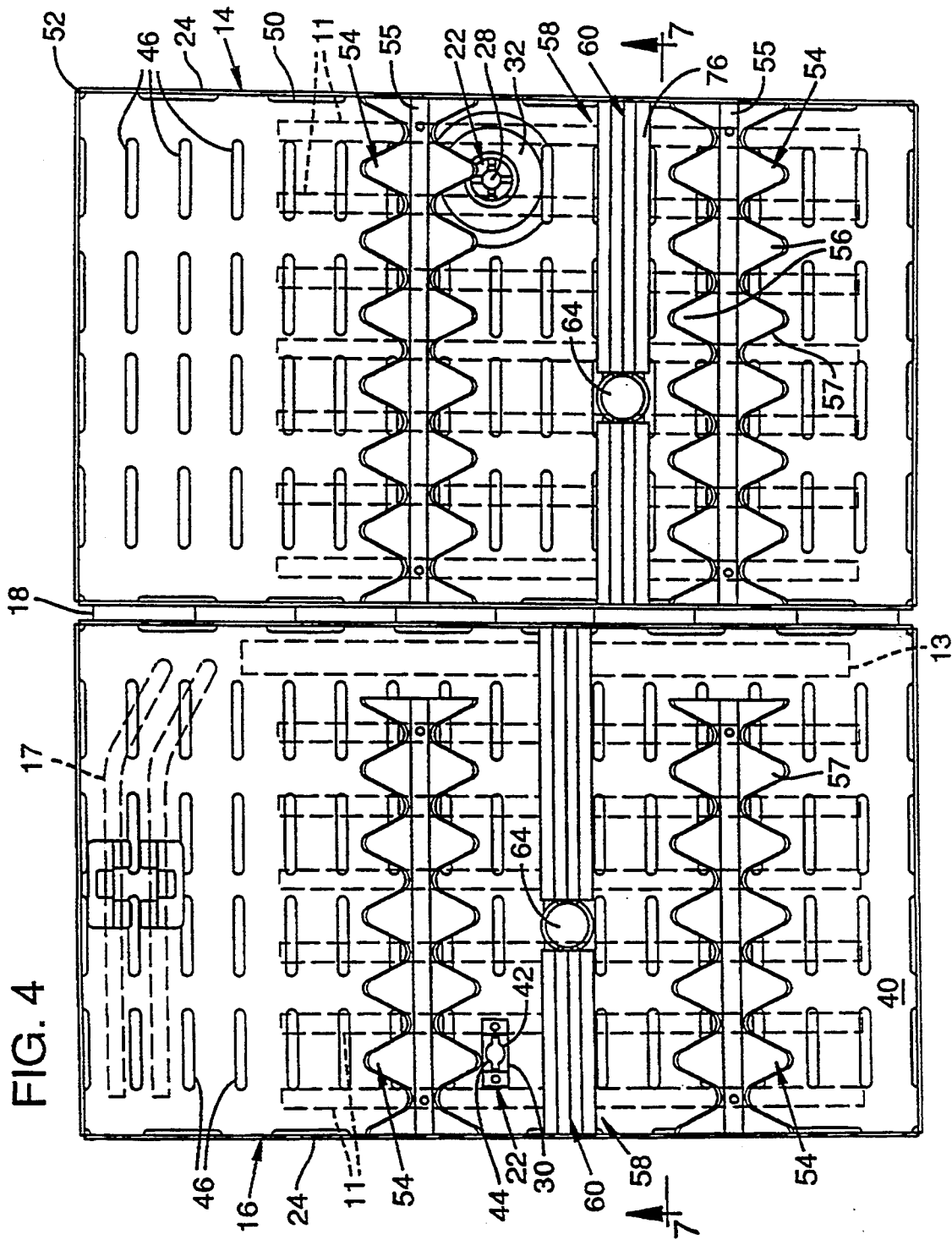
FIG. 4 is a top plan view of the cassette of FIG. 1 in an open configuration.

As shown generally in FIG. 1, a dental instrument sterilization cassette 10 in accordance with a preferred embodiment of the present has a perforated housing 12 including a top cover 14 hinged at 18 to a bottom tray 16. Drainage openings are provided through the perforated housing top and bottom walls, front and back walls, edges, and corners. A internal cassette latching mechanism 22 structurally defines cover 14 with a cover-located, protectively recessed latch actuator 26. Within housing 12, dental instruments are secured within cradle supports 54 by holddown devices 58, which are provided in both tray 16 and cover 14.

The instrument sterilization cassette of the illustrated embodiment is generally rectangular with the cover 14 constituting the upper half, and the tray 16 constituting the lower half, of the perforated housing 12. When the cover 14 is closed upon the tray 16, the perforated housing presents top and bottom walls 34, 48 defined by the horizontal walls of the cover 14 and the tray 16, respectively. Perforated housing front and rear walls 24, 20 are defined by the co-planar, abutting longitudinal rim walls of the cover and tray 16, and the perforated housing side walls 19, 21 are defined by the co-planar, abutting lateral rim walls of the cover 14 and tray 16.

A piano-type hinge 18 connects the cover 14 and the tray 16 along substantially the entire length of the rear wall 20 of the perforated housing 12, (see FIGS. 2 and 3). The hinge 18 is integral with the perforated housing 12, being constructed from closely-interspersed tabs extending from the abutting longitudinal rear rim walls of the cover 14 and tray 16. The tabs are bent over an elongated hinge rod 23 to provide the hinge 18. Such an integrally-constructed hinge 18 minimizes the need for welds and fasteners in the sterilization cassette 10.

To enable an effective flow of sterilizing fluid through the cassette, as well as efficient debris drainage during instrument sterilization, the top, bottom, front, and rear walls of both the cover and tray are perforated. As illustrated in FIG. 1, the perforated housing has a top wall 34 and bottom 48 (not shown) provided with rows of slotted openings 46. In order to maximize sterilizing vapor circulation through the housing, while minimizing the risk of accidental instrument protrusion through an opening, narrow but long (i.e., 3/32×¾ inch) slotted openings are preferred. To further reduce the chance of accidental instrument exposure, the elongated slotted openings are oriented perpendicular to the front and rear walls 20, 24 of the perforated housing 12. In addition, the perforated housing front and rear walls 20, 24 each have rows of slotted openings 46. To provide for the narrow but long slotted opening dimensions on these narrow surfaces, the openings are oriented parallel to the top wall 34 and bottom wall 48. Slotted edge openings 50 are provided along all of the edges of the perforated housing. Additionally, the perforated housing 12 is provided with open corners 52. This pattern of openings through the perforated housing's edges and corners improves drainage by minimizing the locations where instrument debris may tend to accumulate. Side walls 19, 21 are unslotted to prevent the tips of instruments within the cassette from protruding accidentally through such walls.

As shown in FIGS. 1 and 3, a latching mechanism 22 for latching the cover 14 upon the tray 16, is situated adjacent the front wall 24 of the perforated housing 12. As best shown in FIG. 8, the latching mechanism 22 comprises a latch actuator 26 with a latch stem 28 extending thereunder, and a latch anchor 30. The latch actuator 26 is rotatably housed in a protective recess 32 provided on the top wall 34, adjacent the front wall 24.

By recessing the latch actuator 26 within the top wall 34, the cover 14 and therefore the correct upright orientation of the cassette, are structurally defined. The advantage of this placement of the latch actuator 26 is apparent when the cassette is resting in a cover-down orientation on a surface. In this condition the latch actuator 26 is impossible to reach and release. Therefore, this embodiment of the latch actuator 26 makes an inadvertent "upside-down" opening of the instrument cassette very unlikely.

The latch stem 28 extends rigidly downward from a rivet-type attachment to the latch actuator 26. The latch stem 28 is rotatably held within an opening centrally provided in the recess 32. The latch stem 28 is confined in the opening by the latch actuator 26 situated above, and a lock-type washer 29 situated below the opening in the recess 32. The distal end of the latch stem 28 is provided with latch teeth 38. When the perforated housing 12 is in a closed position, the latch stem 28 extends into the interior of the perforated housing 12, where the latch teeth 38 are received by a latch anchor 30.

In the illustrated embodiment, the latch anchor 30 is an inverted U-shaped structure. The distal ends of the inverted "U"'s legs are attached by spot welds to the tray interior 40. The lateral section at the top of the inverted "U" is a latch anchor face 42, provided with a latch opening 44. The latch opening 44 (FIG. 4) is profiled as a "double keyhole" opening with opposed narrow slots extending in opposite directions from a large central opening to receive the latch teeth 38 when they are in a released position aligned in register with the slots. In the illustrated embodiment, two released positions exist, each corresponding to the latch actuator 26 being positioned perpendicular to the front wall 24 of the perforated housing 12. With the latch teeth received in the slots of the latch opening 44, the latching mechanism is positively locked by rotating the latch actuator 26 away from a position perpendicular to the front wall 24. Hereby, the latch teeth 38 are rotated away from beneath the slots of the open profile of the latch opening 44, into a latched condition beneath the latch anchor face 42. Given the recessed location, and the rotation required to release the latch actuator 26, the chance of accidental latch release is minimized.

While the illustrated latching mechanism is a preferred embodiment, it should be understood that alternative locking or positive latching mechanisms may work equally as well. For example, a threaded stem could be used to engage a latch anchor, instead of the latch teeth. Other possibilities include latching mechanisms, and variations thereof, which are positive and offer a recessed, rotatable, and cover-defining latch actuator.

Within the perforated housing 12, the illustrated embodiment provides for dental instrument storage in both the cover 14 and tray 16, as best shown in FIG. 4. Two rows of cradle supports 54 are attached by spot welds to both the cover 14 and the tray 16. The cradle supports 54 extend laterally across both the cover and tray and are configured to loosely support dental instruments 11 of various sizes.

As seen in FIGS. 4 and 7, each cradle support 54 is comprised of a single piece of metal, with an elongated central attachment strip 55 providing a surface for spot welding or other attachment to the interior of the cover 14 or tray 16. On each side of the attachment strip 55, the metal of the cradle support 54 is bent upwardly at about a 50 degree angle to form a pair of oppositely disposed cradle plates 56. Each cradle plate 56 is provided with an identical series of open, upwardly oriented notched cradles 57. Thus, a series of identical pairs of notched cradles is present along the cradle support 54.

In both the cover 14 and the tray 16, two identical cradle supports 54 are present. The two cradle supports 54 are secured into the cover or tray so that the pairs of notched cradles 57 on the first cradle support 54 alignedly correspond to the pairs of notched cradles 57 on the other cradle support.

The cradle supports 54 may extend completely across the perforated housing 12, as shown in the cover 14 illustrated in FIG. 4. Alternatively, the cradle supports 54 may extend partially across the perforated housing, as shown in the tray 16 of FIG. 4, in order to enable storage of large diameter dental instruments 13 directly on the tray. In addition, an end of the tray 16 may be provided with specialized clips 15 to secure dental syringes 17.

To secure the dental instruments 11 snugly within the cradled supports 54, a holddown device 58 is provided within the cover 14 and the tray 16. As best illustrated in FIG. 5, the holddown device 58 has a retention bar 60, which rotatably houses an actuator assembly 62 made up of an actuator knob 64 disposed above, and a toothed stem 66 extending beneath, the retention bar 60.

The holddown device's retention bar 60 provides snug retention of variously sized dental instruments within the cradled supports 54. As best illustrated in FIGS. 5 and 6, the retention bar 60 is constructed of two resilient sleeves 76, which envelop and hold in parallel relationship two rods 74. The resilient sleeves 76 each have two longitudinal rod holes 79 (see FIG. 6) to snugly receive the pair of parallel rods 74. One sleeve 76 is installed over each end of the pair of parallel rods 74, so that the sleeves 76 envelop all but a central bowed portion 75 of each rod 74. Between the resilient sleeves 76 at the central location, an actuator assembly 62 is held between the rods 74. Running the length of the resilient sleeve 76 are several longitudinal ridges 78, whose instrument retaining purpose will be discussed below.

The actuator assembly 62 is rotatably held between the rods 74 of the retention bar 60 by the bowed rod portions 75, the rods 74 together bowing outwardly around and partially encircling the actuator assembly 62. As shown in FIG. 5, the actuator assembly 62 is rotatably confined within the bowed portions 75 of the rods, by an actuator knob 64 situated above, and an actuator lock washer 65 situated below, the bowed portions 75. On either side of the actuator assembly 62, the rods are bent downwardly a few degrees, providing a leaf-spring effect for instrument retention purposes to be described below.

This preferred mode of retention bar 60 construction is advantageous. For instance, the rods' 74 attachment within the resilient sleeves 76 holds the retention bar together, and helps secure the retention bar's 60 attachment to the actuator assembly 62. Hereby, the need for fasteners in the preferred embodiment is minimized.

As shown in FIG. 7, the retention bar 60 is attached over the cradled dental instruments 11 by inserting the actuator assembly's toothed stem 66 into a holddown anchor 68 attached within the tray 16 and the cover 14. The holddown anchor 68, much like the latch anchor 30, is spot welded into the tray 16, and has a holddown opening 70 profiled to receive the toothed stem 66. With the toothed stem 66 received through the holddown opening 70, the actuator knob 64 is rotated to move the toothed stem 66 into a locked condition beneath the holddown anchor face 72. Hereby, the retention bar 60 is positively secured atop the dental instruments 11 lying in the cradle supports 54.

Once so secured atop the cradled instruments 11, the retention bar 60 provides an effective dual method for retaining the instruments. Firstly, the resilient sleeve's ridges 78 resiliently conform to the various dimensions of different dental instruments resting within the cradle supports 54. In addition, the downward bending of the retention bar rods 74 applies a leaf-spring type retaining force to the instruments 11, urging them firmly against cradles 57. This combination of leaf-spring and resilient sleeve retention, further in combination with the openness of the cradle supports 54, enables the secure retention of a wide variety of sizes of instruments 11. This flexibility in retention allows varied combinations of instruments to be securely stored within the perforated housing, all without a need for additional specialized supports or holddowns.

It should be apparent that other retention devices which are not illustrated may work equally as well. For instance, the retention device could include retention bars which are not removable, but which rotate 90° about an anchor to allow instrument storage and removal. Additional possibilities includes any system capable of securely retaining an arbitrary range of dental instrument sizes, when the cassette is in either an opened or closed condition.

Additionally, as illustrated in FIG. 4, the holddown devices 58 in the cover 14 and tray 16 are offset with respect to each other. The offset assures non-interference between the holddown devices as the cover 14 is closed upon the tray 16. This non-interference permits the use of a shallow cover 14 and tray 16, thereby enabling a thin instrument sterilization cassette, with an improved stacking efficiency.

Finally, the cassette of the illustrated embodiment, with versatile instrument storage in both the tray 16 and cover 14, provides for efficient instrument serving in the operating theatre. With the removable bars 60 removed from an open cassette loaded with sterilized instruments 11, the cassette serves the instruments to either a dental assistant or dentist engaged in treatment. The cradle supports 54 enable easy instruments removal for this purpose. It is to be appreciated that the cassette could also sterilize medical instruments and serve them in a medical operating theatre.

Given the cassette's exposure to elevated temperatures, sterilization agents, and frequent use, the choice of materials is important in providing a high level of cassette durability and reliability. To provide optimal integrity and durability, the preferred embodiment's perforated housing 12 is constructed of a stainless steel. This represents an improvement over cassettes which employ degradation-prone plastic housings. In order for the rods 74 to provide a leaf-spring type resilience, the rods are preferably made of a stainless steel which will flex without permanent deformation. Other materials with these same characteristics may also be suitable for use in the rods 74. To withstand elevated temperatures, and the corrosive effect of sterilization agents, the resilient sleeves 76 are preferably an extrusion made of a heat- and corrosion-resistant resilient silicone rubber. The use of resilient plastic with similar qualities is also a possibility.

This detailed description is set forth only for purposes of illustrating examples of the present invention and should not be considered to limit the scope of the invention in any way. Clearly numerous additions, substitutions, and modifications can be made to these examples without departing from the scope of the invention which is defined by the appended claims and their equivalents.

I claim:

1. An instrument sterilization cassette comprising:
   a housing having a tray and a cover;
   a first instrument support means mounted in the tray, and a second instrument support means mounted in the cover; said instrument support means each for longitudinally supporting a plurality of instruments and
   a transverse holddown bar removably mounted solely by a single-point, manually rotatable latch to a support anchor mounted in the cover to hold instruments within the second instrument support with the cover open and closed, the holddown being selectively detachable and removable in its entirety from the cover by rotation of the latch to permit unobstructed access to instruments stored in the second instrument support when the cover is open.

2. An instrument sterilization cassette according to claim 1, wherein the latch has a thumb knob to facilitate manual rotation of the latch with one hand to remove and install the holddown in the cover.

3. An instrument sterilization cassette according to claim 1, wherein the first instrument support has a series of cradles extending transversely across the tray, and the latch and support anchor in the cover are positioned between two adjacent cradles of the first instrument supports when the cover is closed over the tray, such that the latch is received between adjacent cradles of the first instrument support to prevent the latch from conflicting with instruments within the cradles and permit a low-profile cassette when the cover is closed.

4. An instrument sterilization cassette according to claim 1, wherein the tray and cover are inseparably connected by a piano-type hinge.

5. An instrument sterilization cassette according to claim 1, wherein the tray and cover form solid side walls at opposing longitudinal ends of the cassette when the cover is closed on the tray, in order to prevent any sharp ends of instruments held in the cassette from protruding from the closed cassette.

6. An instrument sterilization cassette according to claim 1, wherein
   the tray forms a planar bottom wall of the cassette and the cover forms a planar top wall of the cassette, and the top wall defines a recess extending inwardly from its outer surface;
   a latching mechanism is provided entirely on the inside of the tray and cover to latch the tray and cover together in a closed position; and
   a latch actuator housed entirely within the recess is connected to the latching mechanism and movable within the recess to latch and unlatch the latching mechanism, the recess protecting the latch actuator from accidental movement, and the latch actuator serving as a visual indicator to distinguish the cover from the tray such that the cover is not opened upside down.

7. An instrument sterilization cassette according to claim 6, wherein a single latching mechanism and latch actuator are provided on the cassette.

8. An instrument sterilization cassette according to claim 1, wherein the holddown includes an elongate spring with the latch rotatably mounted between the opposite ends thereof, the spring extending transversely across the cover when the holddown is attached to the cover, and the elongate spring being angled toward the interior of the cover on either side of the latch to resiliently urge instruments within the instrument support.

9. An instrument sterilization cassette according to claim 8, wherein the spring is substantially entirely enveloped in a resilient sleeve, the sleeve holding the spring and latch together.

10. An instrument sterilization cassette according to claim 8, wherein the spring comprises a plurality of stiff but resilient elongate rods.

11. An instrument sterilization cassette according to claim 10, wherein the rods have outwardly bowed central portions that rotatably mount the latch.

12. An instrument sterilization cassette comprising:
a perforated housing for housing instruments to be sterilized, said housing having a cover hingedly closable on a tray to define a top planar wall on the cover, and a bottom wall on the tray;
a first instrument support mounted transversely across the inside of the tray to receive and support instruments in the tray and a second instrument support mounted transversely across the inside of the cover to receive and support additional instruments in the cover;
a first elongate holddown bar transversely mountable across the inside of the tray to hold instruments within the first instrument support within the tray, the first holddown bar having a sole first single-point, centrally located rotatable stem with a first thumb knob, the first stem being lockably engagable with a first holddown anchor mounted within the tray, the first stem being selectively rotatable to an unlock position to release the first holddown bar from the first holddown anchor to permit complete removal of the first holddown bar from the cassette;
a second holddown bar transversely mountable across the inside of the cover to hold additional instruments within the second instrument support within the cover, the second holddown bar having a sole second single-point, centrally located rotatable stem with a second thumb knob, the second stem being lockably engagable with a second holddown anchor mounted within the cover, the second stem being selectively rotatable to an unlock position to release the second holddown from the second holddown anchor to permit the complete removal of the second holddown bar from the cassette;
the top wall defining a recess extending inwardly from an outside surface thereof;
a latch actuator being rotatably mounted and completely recessed within the recess; and
a latch stem fixedly attached to the latch actuator and extending entirely within the housing when the cover is closed on the tray, a latch anchor mounted to the inside of the tray to receive the latch stem, and the latch actuator being selectively rotatable within the recess to rotate the latch stem to locked and unlocked positions within the latch anchor.

* * * * *